(12) United States Patent
Wu et al.

(10) Patent No.: US 8,895,261 B2
(45) Date of Patent: Nov. 25, 2014

(54) USE OF FLUORESCENT SACCHARIDE-BASED DERIVATIVE

(71) Applicant: I-Shou University, Kaohsiung (TW)

(72) Inventors: Jau-Yann Wu, Kaohsiung (TW);
Li-Feng Liu, Kaohsiung (TW);
Kuan-Ju Pan, Kaohsiung (TW);
Hao-Yu Tseng, Kaohsiung (TW);
Jian-Ching Wu, Kaohsiung (TW)

(73) Assignee: I-Shou University, Kaohsiung (TW)

( * ) Notice: Subject to any disclaimer, the term of this patent is extended or adjusted under 35 U.S.C. 154(b) by 0 days.

(21) Appl. No.: 13/802,626

(22) Filed: Mar. 13, 2013

(65) Prior Publication Data

US 2014/0113325 A1    Apr. 24, 2014

(30) Foreign Application Priority Data

Oct. 23, 2012    (TW) .............................. 101139123 A

(51) Int. Cl.
| | | |
|---|---|---|
| *C12Q 1/04* | (2006.01) | |
| *C12Q 1/02* | (2006.01) | |
| *G01N 33/94* | (2006.01) | |
| *G01N 33/50* | (2006.01) | |

(52) U.S. Cl.
CPC ...... *C12Q 1/04* (2013.01); *C12Q 1/025* (2013.01); *G01N 33/94* (2013.01); *G01N 33/5091* (2013.01); *G01N 33/50* (2013.01); *C12Q 1/02* (2013.01)
USPC .......................................................... 435/34

(58) Field of Classification Search
None
See application file for complete search history.

(56) References Cited

U.S. PATENT DOCUMENTS

| | | | |
|---|---|---|---|
| 5,633,351 A | | 5/1997 | Reed |
| 7,911,617 B2* | | 3/2011 | Padmanabhan et al. ...... 356/450 |
| 2009/0317829 A1 | | 12/2009 | Thorson et al. |
| 2012/0245054 A1* | | 9/2012 | Thorson et al. ................. 506/10 |
| 2012/0267572 A1* | | 10/2012 | Wu et al. ..................... 252/301.16 |

FOREIGN PATENT DOCUMENTS

TW          201243019          11/2012

OTHER PUBLICATIONS

Hassanein, M., Weidow, B., Koehler, E. Bakane, N., Garbett, S., Shyr, Y., and Quaranta, V. "Development of High-Throughput Quantitative Assays for Glucose Uptake in Cancer Cell Lines", Molecular Imaging and Biology 2011, vol. 13, pp. 840-852.*
K. S. Chio, et al., "Synthesis and Characterization of the Fluorescent Products Derived from Malonaldehyde and Amino Acids," Biochemistry, Jul. 1969, vol. 8, No. 7, pp. 2821-2827.
"Office Action of Taiwan Counterpart Application", issued on May 26, 2014, p. 1-7.

* cited by examiner

*Primary Examiner* — L B Driscoll
*Assistant Examiner* — Michelle F Paguio Frising
(74) *Attorney, Agent, or Firm* — Jianq Chyun IP Office

(57) ABSTRACT

The disclosure provides a use of a fluorescent saccharide-based derivative in cell detection. The fluorescent saccharide-based derivative is obtained from a reactive material through an imine formation reaction, and the reactive material is selected from a composition (A) or a composition (B). The composition (A) includes a reducing sugar compound and an amino group-containing compound having at least one primary amino group. The composition (B) includes an amino sugar compound and a carbonyl group-containing compound, and the amino sugar compound contains at least one primary amino group.

11 Claims, 17 Drawing Sheets
(8 of 17 Drawing Sheet(s) Filed in Color)

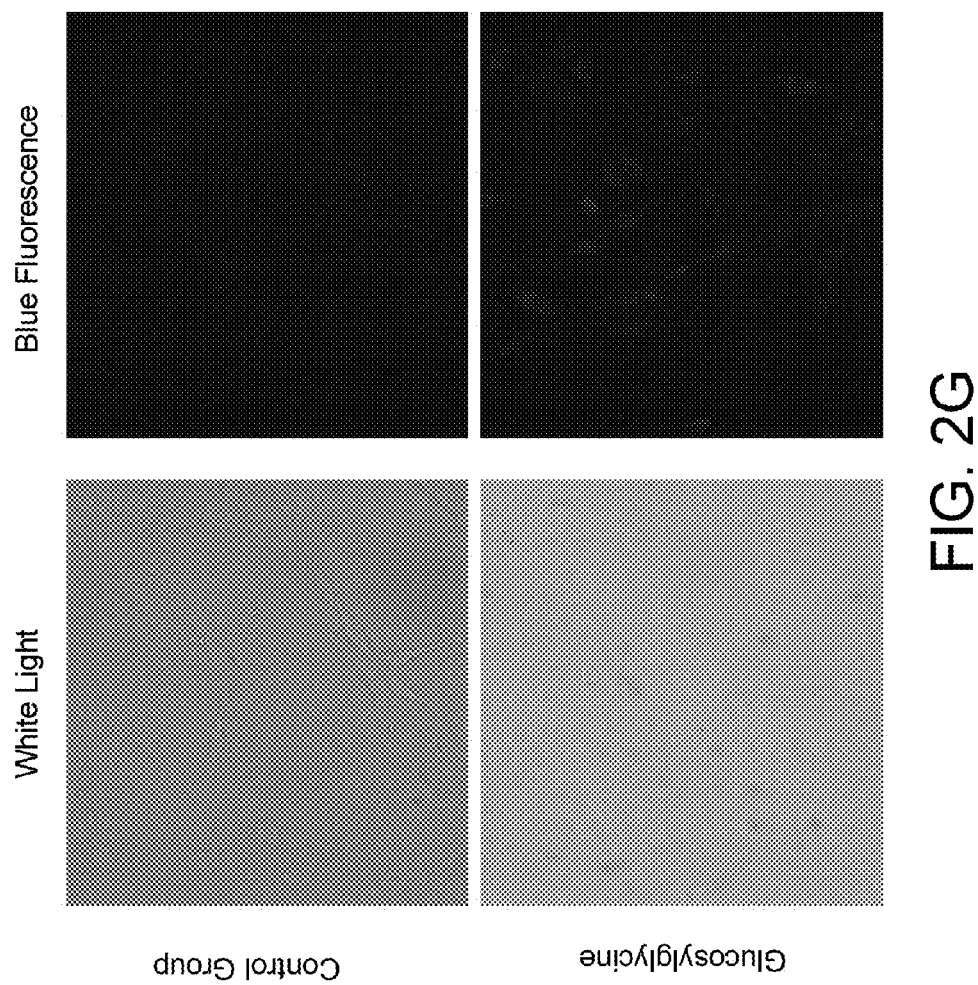

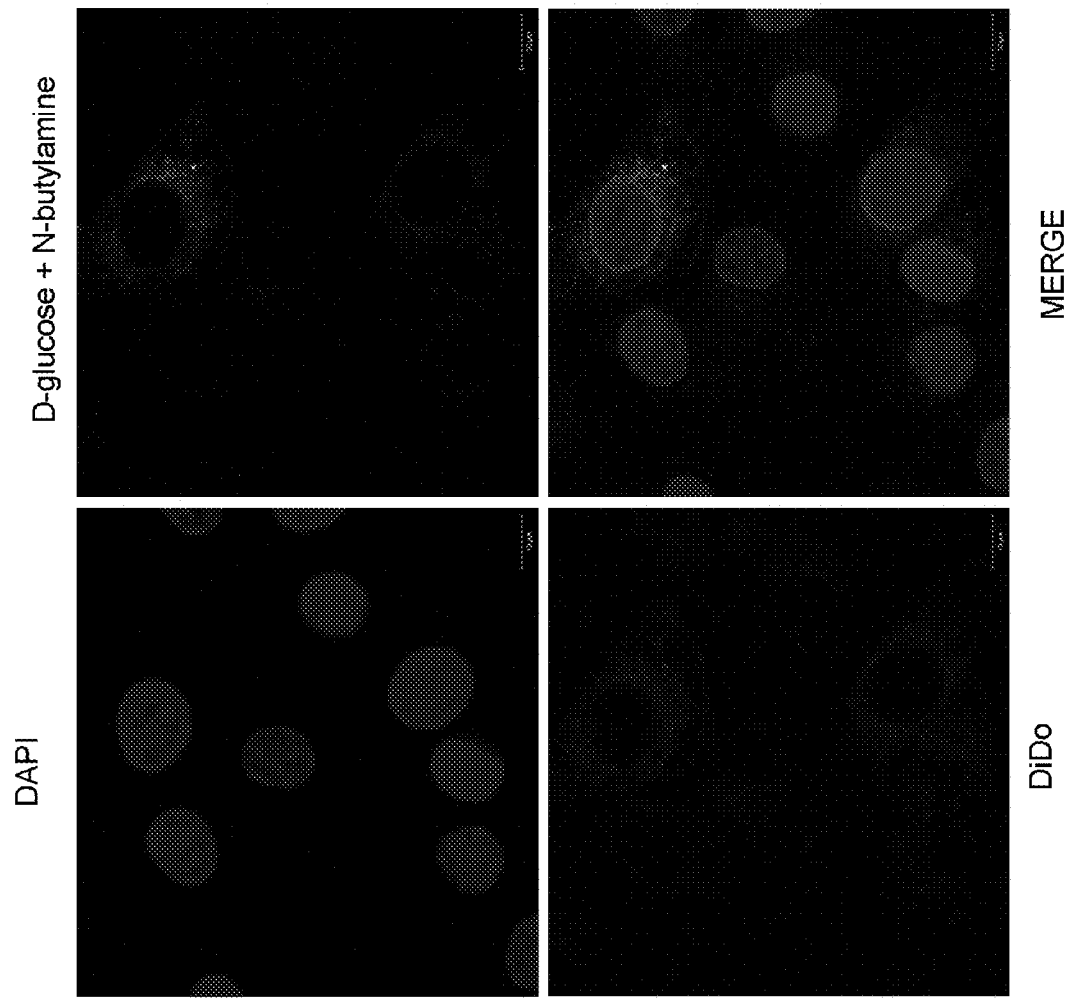

USE OF FLUORESCENT SACCHARIDE-BASED DERIVATIVE

CROSS-REFERENCE TO RELATED APPLICATION

This application claims the priority benefit of Taiwan application serial no. 101139123, filed Oct. 23, 2012. The entirety of the above-mentioned patent application is hereby incorporated by reference herein and made a part of this specification.

BACKGROUND OF THE INVENTION

1. Field of the Invention

The disclosure relates to a use of a saccharide-based derivative in the field of biomedical detection, and more particularly, to a use of a fluorescent saccharide-based derivative.

2. Description of Related Art

Currently, with increasing demands of health care and medical services, the development of biomedical sensing techniques has become important. In most biomedical imaging techniques, non-invasive optical sensing methods are often used to detect and track cells or molecules to help diagnose diseases.

Saccharide-based molecules are one of the main energy sources of cells, and play an important role in the disease progression of cancer and microbial infections. Moreover, many saccharide-based cell markers are currently being used to detect various diseases. Previous research shows that most cancer cells take up more saccharide-based molecules than normal cells. Therefore, observing the situation of cells taking up saccharides helps to detect proliferation, differentiation, metastasis and blood vessel angiogenesis of cancer cells.

One of the main and current diagnostic tools for detecting cancer and diseases of the brain and the heart is positron emission tomography (PET). In position emission tomography, saccharide-based molecules containing positron isotope markers (for instance, fluorine-18-fluorodeoxyglucose; FDG) may, for instance, be used as a radiocontrast agent to perform non-invasive detection on tissues.

However, since the positron isotope in the radiocontrast agent has to be fabricated in a cyclotron, and the positron isotope has a short half-life (for instance, the half-life of fluorine-18 is about two hours), the positron emission topography equipment has to be set up near the cyclotron in order to quickly obtain the contrast agent. Moreover, large amounts of radiation are released during position emission topography, and its radiation dose may even be dozens of times to hundreds of times larger than that of regular X-ray; therefore, it may cause cell damage, and the damage done to reproductive systems of young females is particularly appalling. Moreover, since the positron emission topography equipment and the cyclotron facility are very expensive, the detection fees are consequently also high.

Moreover, it is necessary to develop a particular fluorescent detection system with features of simple, low cost, good biocompatibility, less toxic, etc. and is applicable to fields such as clinical disease detection and drug screening.

SUMMARY OF THE INVENTION

The disclosure provides a use of a fluorescent saccharide-based derivative in cell detection that reduces detection costs, does not need to use expensive instruments or equipment, and has no risk of being exposed to high-energy radiation.

The disclosure provides a use of a fluorescent saccharide-based derivative in cell detection. The fluorescent saccharide-based derivative is obtained from a reactive material through imine formation reaction, and the reactive material is selected from the following composition (A) or composition (B):

The composition (A) contains a reducing sugar compound and an amino group-containing compound, and the amino group-containing compound contains at least one primary amino group; the composition (B) contains an amino sugar compound and a carbonyl group-containing compound, and the amino sugar compound contains at least one primary amino group.

In an embodiment of the disclosure, the reducing sugar compound is selected from the group consisting of glucose, maltose, fructose, lactose, galactose, mannose, cellobiose, xylose, arabinose, ribose, deoxy ribose, dextrin, D-glucosamine and N-acetyl-glucosamine.

In an embodiment of the disclosure, the amino group-containing compound is selected from an amino acid or an alkyl amine.

In an embodiment of the disclosure, the amino group-containing compound is selected from the group consisting of butylamine, octylamine, 1-dodecylamine, 1-hexadecylamine, 1,6-hexadiamine, glycine, alanine, valine, leucine, isoleucine, phenylalanine, tryptophan, tyrosine, aspartic acid, histidine, asparagine, glutamic acid, lysine, glutamine, methionine, arginine, serine, threonine, cysteine, and proline.

In an embodiment of the disclosure, the amino sugar compound is selected from the group consisting of D-glucosamine, galactosamine, and chitosan.

In an embodiment of the disclosure, the carbonyl group-containing compound is selected from the group consisting of acetone, isovaleraldehyde, D-glucosamine, and N-acetyl-glucosamine.

In an embodiment of the disclosure, the amino sugar compound and the carbonyl group-containing compound are the same compound.

In an embodiment of the disclosure, the fluorescent saccharide-based derivative is used to detect cancer.

In an embodiment of the disclosure, the fluorescent saccharide-based derivative is used to detect microorganisms.

In an embodiment of the disclosure, the fluorescent saccharide-based derivative is used to screen drugs related to regulation of the ability of cells to take up saccharides.

In an embodiment of the disclosure, the fluorescent saccharide-based derivative is used to detect environmental toxicants.

Based on above, the use of a fluorescent saccharide-based derivative in cell detection provided in the disclosure may achieve a fluorescent detection mechanism that is fast, simple, low costing, non-toxic, and has good biocompatibility, thus is ideal for disease detection, microorganism detection, simple environmental toxicant detection, drug screening, etc.

In order to make the aforementioned features and advantages of the disclosure more comprehensible, embodiments accompanied with figures are described in detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2G shows images observed under a fluorescent microscope of using a prepared fluorescent saccharide-based derivative according to an embodiment of the disclosure in a cell uptake experiment.

FIG. 3 shows images observed under a laser confocal microscope of using a fluorescent saccharide-based derivative obtained from a reaction between D-glucose and n-butylamine in detection of glioma cancer cells from mixed heterogeneous cells according to an embodiment of the disclosure.

DESCRIPTION OF THE EMBODIMENTS

Figure 1A:
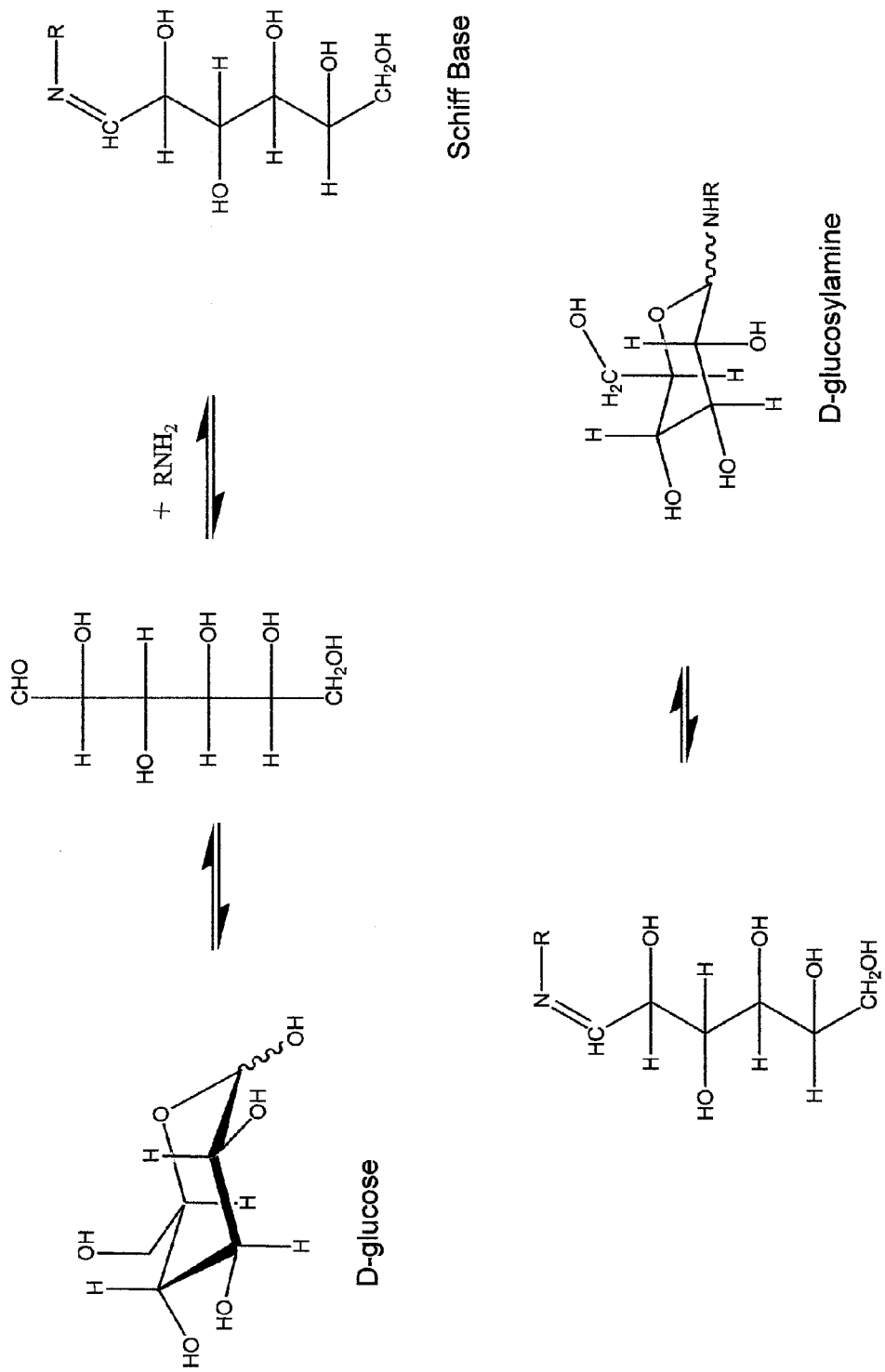
FIG. 1A is a schematic diagram of the reaction mechanism for preparing fluorescent saccharide-based derivatives according to an embodiment of the disclosure.

The disclosure provides a use of a fluorescent saccharide-based derivative. The fluorescent saccharide-based derivative is obtained from a reactive material through an imine formation reaction, and the reactive material is selected from composition (A) or composition (B). The composition (A) includes a reducing sugar compound and an amino group-containing compound, and the amino group-containing compound contains at least one primary amino group; the composition (B) includes an amino sugar compound and a carbonyl group-containing compound, and the amino sugar compound contains at least one primary amino group.

In particular, at least one imino group (C=N) is formed from the reactive material after the imine formation reaction. Specifically, the imino group is, for instance, an aldimino group and/or a ketimino group.

In the following, the composition of the fluorescent saccharide-based derivative used in the disclosure is explained, followed by the principles and the applications of the disclosure described in detail with various embodiments. It should be noted that, in the specification, if it is not specifically described that a compound is substituted or not, then it should be explained that the compound includes both a compound without substituents and a compound containing substituents. For instance, the term 'primary amine' includes primary amine and substituted primary amine.

Composition (A)

The composition (A) includes a reducing sugar compound and an amino group-containing compound having at least one primary amino group.

The reducing sugar compound is a compound containing an aldehyde group or a keto group, and has reducing ability, including monosaccharide, disaccharide, oligosaccharide, and polysaccharide. In particular, the reducing sugar compound is, for instance, selected from the group consisting of glucose, maltose, fructose, lactose, galactose, mannose, cellobiose, xylose, arabinose, ribose, deoxy ribose, dextrin, D-glucosamine, and N-acetyl-glucosamine, but is not limited to the above compounds.

The amino group-containing compound is a compound having at least one primary amino group that is selectable from either an amino acid or an alkyl amine. In particular, the amino group-containing compound is, for instance, selected from the group consisting of butylamine, octylamine, 1-dodecylamine, 1-hexadecylamine, 1,6-hexadiamine, glycine, alanine, valine, leucine, isoleucine, phenylalanine, tryptophan, tyrosine, aspartic acid, histidine, asparagine, glutamic acid, lysine, glutamine, methionine, arginine, serine, threonine, cysteine, and proline. However, it is not in actuality limited to the above compounds.

In the composition (A), the contents of the reducing sugar compound and the amino group-containing compound are not particularly limited as long as the imino group is produced in accordance with demand. The mole ratio of the reducing sugar compound and the amino group-containing compound is, for instance, set in the range of 1:20 to 20:1, but is not limited thereto.

The composition (A) may selectively include an appropriate solvent to make the reducing sugar compound and the amino group-containing compound dissolve in the solvent to conduct the imine formation reaction. The type of solvent may be selected according to the experimental condition and the type of compound, and is not particularly limited. Moreover, the environmental conditions (for instance, the temperature and pressure parameters) of the imine formation reaction may also be adjusted according to demand for assisting in forming the fluorescent saccharide-based derivative used in the disclosure.

In particular, concerning the stability of the reaction rate and the reaction products, pH of the reaction may, for instance, be controlled in a slightly alkaline environment during the imine formation reaction, and the temperature may be controlled between 25° C. to the reflux temperature of the composition (A) in order to easily obtain the desired fluorescent saccharide-based derivative.

Composition (B)

The amino sugar compound is, for instance, selected from the group consisting of D-glucosamine, galactosamine, and chitosan, but is not limited thereto. The carbonyl group-containing compound is, for instance, selected from the group consisting of acetone, isovaleraldehyde, D-glucosamine, and N-acetyl-glucosamine, but is not limited thereto.

Similarly, the contents of the amino sugar compound and the carbonyl group-containing compound in the composition (B) are not particularly limited as long as the imino group is produced in accordance with demand. The mole ratio of the amino sugar compound and the carbonyl group-containing compound is, for instance, set in the range of 1:20 to 20:1, but is not limited thereto.

The composition (B) may selectively include an appropriate solvent to make the amino sugar compound and the carbonyl group-containing compound dissolve in the solvent to conduct the imine formation reaction. The type of solvent may be selected according to the experimental condition and the type of compound, and is not particularly limited. Moreover, the environmental conditions (for instance the temperature and pressure parameters) of the imine formation reaction may also be adjusted according to demand for assisting in forming the fluorescent saccharide-based derivative used in the disclosure.

In particular, concerning the stability of the reaction rate and the reaction products, pH of the reaction may, for instance, be controlled in a slightly alkaline environment during the imine formation reaction, and the temperature may be controlled between 25° C. to the reflux temperature of the composition (B) in order to easily obtain the desired fluorescent saccharide-based derivative.

It is worth noting that, the amino sugar compound and the carbonyl group-containing compound in the composition (B) may be the same compound. That is, the desired fluorescent saccharide-based imino derivative may be formed by a self reaction of an amino sugar compound containing a carbonyl group. The amino sugar compound containing a carbonyl group is, for instance, D-glucosamine, but is not limited thereto.

Moreover, since the fluorescent saccharide-based derivative used in the disclosure is applied in detection of cells, it is preferred that the reducing sugar compound, the amino group-containing compound, the amino sugar compound, and the carbonyl group-containing compound are free of biological toxicity and have good biocompatibility. Moreover, having a structure which is able to selectively pass through cell membrane and enter into the cell is also preferred. In particular, the structure may be a structure obtained from transforming a composition, which is formed by subjecting the composition (A) to the imine formation reaction, through cyclization.

Detecting cells with the fluorescent saccharide-based derivative obtained from the reactive material that have good dispersibility in an aqueous environment, good photostability, strong fluorescence and low toxicity, which make them excellent candidates as biological markers.

In the following, the reaction mechanism of the fluorescent saccharide-based derivative of the disclosure is briefly explained through FIG. 1A and FIG. 1B. In particular, FIG. 1A is an example of the composition (A) being used as a reactive material, and FIG. 1B is an example of the composition (B) being used as a reactive material.

Figure 1B:
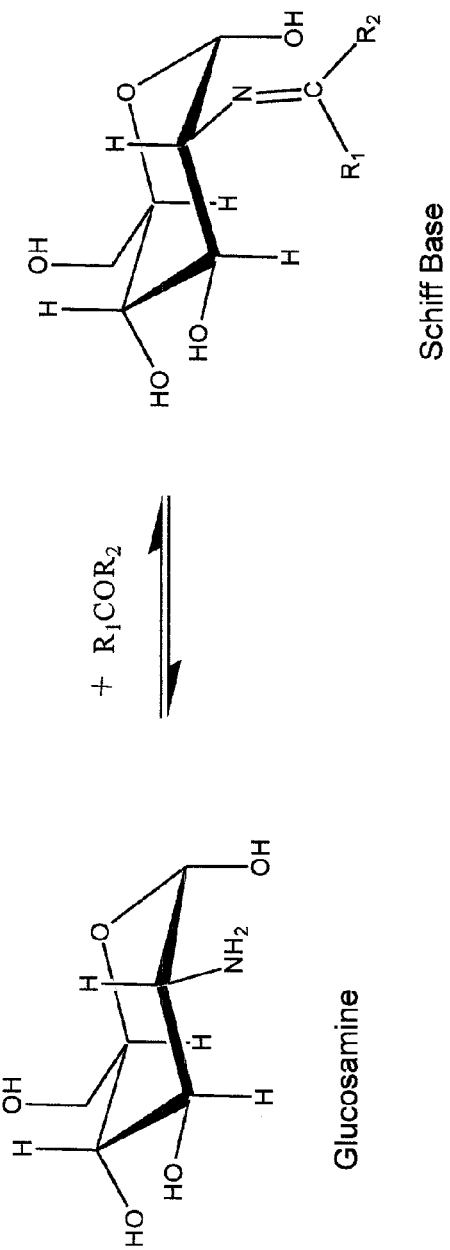
FIG. 1B is a schematic diagram of the reaction mechanism for preparing fluorescent saccharide-based derivatives according to another embodiment of the disclosure.

Referring first to FIG. 1A, the reducing sugar compound used in the embodiment is D-glucose, and the amino group-containing compound is shown with the chemical formula $RNH_2$. Specifically, R represents any organic group that is substituted or not substituted.

The D-glucose is an aldose, which may include ring isomers and open-chain isomers under equilibrium conditions. As shown in FIG. 1A, when D-glucose and the amino group-containing compound mix under an appropriate circumstance as described above, nucleophilic nitrogen atoms in the amino group would attack the carbon in the aldehyde group of D-glucose, and the amino group-containing compound and D-glucose conduct condensation reaction to form an imino group-containing Schiff base after water molecules are removed. It should be noted that, the glucose derivative may exist in both forms of a linear Schiff base and a cyclized D-glucosylamine (that is, the N-substituted glycosylamine), and the two forms may interconvert to reach a balanced relationship.

In particular, the Schiff base includes a fluorescent C=N bond, thus may emit fluorescence when excited by an appropriate wavelength; the cyclized D-glucosylamine has a structure similar to glucose and may enter into the cell through a glucose transporter (GLUT). A portion of the cyclized D-glucosylamine may be converted to the linear Schiff base form after entering the cell and emit detectable fluorescence.

Therefore, with the characteristics of fluorescence and being able to enter cells, the glucose derivative may be utilized to detect the difference of glucose uptake of different cells by detecting the fluorescence intensity of cells. Moreover, since the materials used are all highly biocompatible molecules, they would not cause any damage to human tissue.

Then, referring to FIG. 1B, in this example, glucosamine that may conduct the self-imine formation reaction is used as the amino sugar compound; therefore, the chemical formula $R_1COR_2$ may represent the molecular structure of glucosamine itself or represent other carbonyl group-containing compounds suitable for the disclosure. When $R_1COR_2$ represents other carbonyl group-containing compounds, $R_1$ and $R_2$ may be any organic group that is substituted or not substituted.

As shown in FIG. 1B, glucosamine having a primary amino group may also conduct the reaction mechanism similar to the one shown in FIG. 1A with carbonyl group-containing compounds, thereby forming an imino group-containing Schiff base with fluorescent characteristics. Since the Schiff base configuration derived from glucosamine in FIG. 1B is a slightly modified structure of the original glucosamine molecule and still has a structure quite similar to the original glucosamine molecule, it may also enter cells through the proteins that can transport glucosamine on the cells. Therefore, by detecting the fluorescence intensity of cells, the difference of saccharide uptake of different cells may also be detected. FIG. 1A and FIG. 1B use glucose and glucosamine as examples for explanation, and one of the ordinary skill in the art should understand that the application principles of other fluorescent saccharide-based derivatives of the disclosure are similar, with the only differences being the identified molecules or the transport mechanisms used for passing through cells.

In particular, the fluorescent saccharide-based derivative provided in the disclosure is suitable for use in cancer detection, microorganism detection, screening medications related to regulation of the ability of cells to take up saccharides, etc. The applications are explained in the following, but actual applications are not limited thereto. One of the ordinary skill in the art may be able to further infer other possible implementations.

Cancer Detection

The fluorescent saccharide-based derivative provided in the disclosure may be used to detect cancer cells. Increased glycolysis is present in a wide spectrum of human tumors. In general, cancer cells display increased consumption of glucose to fulfill their energy requirements; therefore, the sugar uptake is more quickly in cancer cells than in normal cells. Moreover, specific cancer cells may have specificities toward specific saccharide-based molecules (for instance the specificity of liver cancer cells towards galactose). Therefore, differentiation between cancer cells and normal cells may be accomplished by utilizing the above characteristic and the fluorescence characteristic of saccharide-based derivatives after modification.

The following Table 1 shows the substrate specificities and various tissue expressions of a plurality of sugar transporters.

TABLE 1

Substrate specificity and tissue expression of sugar transporters.

| Transporter | Substrate | | Tissue | | | | | | | | | |
|---|---|---|---|---|---|---|---|---|---|---|---|---|
| | Glucose | Fructose | Intestine | Kidney | Blood | Liver | Brain | Pancreas | Testicle | Muscle | Heart | Fat |
| SGLT1 | X | | X | X | | | | | | | | |
| SGLT2 | X | | | X | | | | | | | | |
| GLUT1 | X | | | | X | | X | | | | | |
| GLUT2 | X | | X | X | | X | | X | | | | |
| GLUT3 | X | | | | | | X | | X | | | |
| GLUT4 | X | | | | | | | | | X | X | X |
| GLUT5 | | X | X | | | | | | X | X | | |
| GLUT6 | X | | | | X | | X | | | | | |
| GLUT7 | X | X | X | | | | | | X | | | X |
| GLUT8 | X | | | | | | X | | X | | | X |
| GLUT9 | | X | | X | | X | | | | | | |
| GLUT10 | X | | | X | | X | X | X | | X | X | |
| GLUT11 | X | X | | X | | | | | X | X | | X |
| GLUT12 | X | | X | | | | | | | X | | X |
| GLUT14 | X | | | | | | | | X | | | |

Note:
X means the substrate specificity and the expression of sugar transporter in the corresponding tissue (M. B. Calvo et al., *Int. J. Endocrinol.*, 2010, Article ID 205357.)

Many cancers display high rates of sugar uptake, and therefore can be easily discriminated from normal cells. Cancer types suitable for detection through the use of the present disclosure are, for instance, breast cancer, colon cancer, rectal cancer, esophageal cancer, head and neck cancer, lung cancer, lymphoma, melanoma, thyroid cancer, cervical cancer, ovarian cancer, prostate cancer, oral cancer, leukemia, liver cancer, glioma, but are not limited thereto. One of the ordinary skill in the art may be able to determine the applicability according to clinical demand; therefore, it does not need to be limited.

Microorganism Detection

The fluorescent saccharide-based derivative provided in the disclosure may further be used to detect microorganisms. In particular, since sugar is an important energy source for most microorganisms, the fluorescent saccharide-based derivative provided in the disclosure may also be applied to techniques such as detection of food or the simple detection of environmental toxicants to detect microorganisms in food or the environment, and to detect the existence of toxicants or carcinogens in the environment that inhibit microorganism growth. For instance, it is suitable for detecting microorganisms such as *E. coli, Helicobacter pylori, Pseudomonas aeruginosa, Streptococcus, Salmonella, Staphylococcus aureus*, yeast, mold, or for detecting environmental toxicants such as organic substances and heavy metals produced from human factors that are biologically toxic and carcinogenic, such as industrial solvents, raw materials and products of chemical reactions, industrial waste, plant wastewater, pesticides, and heavy metals such as lead and arsenic, but is not limited thereto.

Moreover, one of the ordinary skill in the art may understand that the fluorescent saccharide-based derivative and other experimental conditions may be selected according to the microorganism detected to achieve a more specific detection method.

Drug Screening

The fluorescent saccharide-based derivative provided in the disclosure may further be used to screen drugs related to regulation of saccharides uptake in cells. The saccharide-uptake ability of cells indicated includes increasing or decreasing the cell uptake of saccharides, but is not limited thereto, and may be other regulations.

When applied to screen the drugs, detection and comparison of saccharides uptake may be conducted to select the drugs or to evaluate the relative dosage response of drugs. For instance, the fluorescent saccharide-based derivative of the disclosure may be applied to the drug screening of saccharide metabolism disorders such as diabetes, hypoglycemia, galactosemia, glycogen storage disease, and the drug screening of using saccharide-based molecule uptake blockers in cancer treatment, but are not in actuality limited thereto.

Moreover, one of the ordinary skill in the art may adjust and select the type of drugs, the adding method and other environmental conditions according to actual demand to optimize the screening results.

The following provides experimental examples to explain the disclosure in more detail. It should be noted that, the following experimental examples are only intended to further explain the characteristics of the fluorescent saccharide-based derivative structure used in the disclosure or the results of undergoing specific processes or experiments, and are not to limit the scope of the disclosure.

EXPERIMENTAL EXAMPLE 1

Preparation, Structure Identification and Cellular Uptake of Fluorescent Saccharide-Based Derivative «Preparation of Fluorescent Saccharide-Based Derivative»

The experimental example uses D-glucosylglycine prepared from D-glucose and glycine as a model reaction to verify the existence of imino product and its fluorescence characteristic, and to verify cell uptake. The following shows the expected chemical reaction in the experimental example. An imino-group contained D-glucosylglycine (Schiff base) is formed from D-glucose and glycine, and the cyclized D-glucosylglycine may enter cells and convert back to a linear Schiff base form and emit fluorescence. The following further explains details such as the preparation and structure verification of the fluorescent saccharide-based derivative of the disclosure.

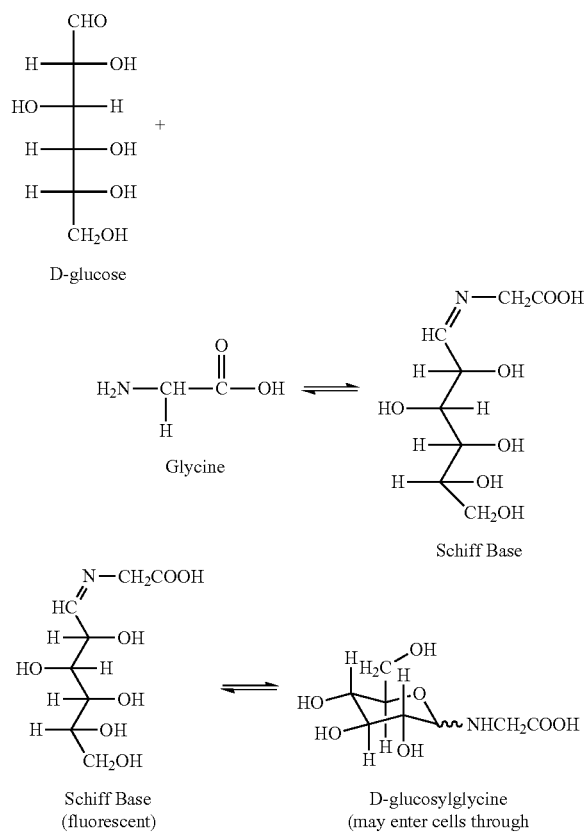

ⓘ indicates text missing or illegible when filed

The materials used in the experimental example include D-glucose, glycine, methanol, and acetone. The preparation steps of the fluorescent saccharide-based derivative are as follows (modified from the procedure of P. S. Song, C. O. Chichester, J. Food Sci. 31 (1966) 914.):

1. Add 75 ml of methanol, 10 g of glucose and 1.4 g of glycine to a round-bottom flask. Conduct reflux stirring for 5 hours.

2. Add 25 ml of methanol and 25 ml of acetone to the reaction solution, apply heat and filter while hot. Collect the filtrate, and add 300 ml of acetone to the filtrate, and place in the refrigerator at 4° C. for 36 hours.

3. Wash the crude product obtained from the filtration repeatedly with a mixed solution composed of 1 to 4 volume parts of methanol to acetone. Heat and dissolve the crude product with adequate amounts of methanol, then filter while hot, and add acetone to the filtrate to recrystallize. After performing suction filtration, wash with the mixed solution, and the end product is obtained after vacuum drying.

«Structure Verification of Fluorescent Saccharide-Based Derivative»

(1) Identification of Molecular Weight

Then, the molecular weight of the end product is identified. The purity and the molecular weight of the product are determined in the experimental example simultaneously with LC/MS. Instruments usage and conditions are as below:

LC (Model: Waters 2695 Separations Module)
  Flow velocity: 0.5 ml/min
  Column: ZORBAX HILIC Plus 4.6×100 mm 3.5 μm
  Mobile phase: 0.4% formic acid in 75% acetonitrile/25% water
MS (Model: Waters micromass ZQ)
ESI-MS (Cone 15 V, 25 V, 50 V)

Figure 2A:
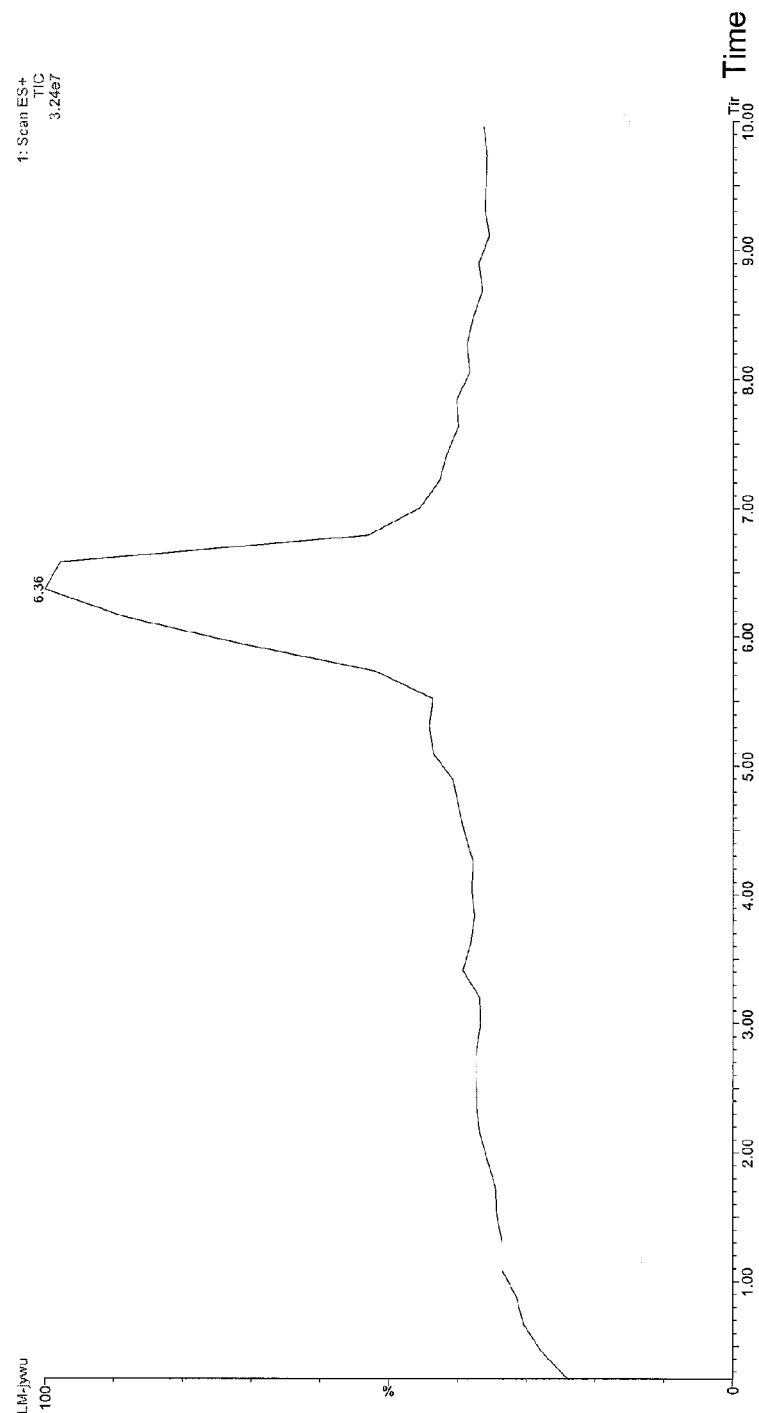
FIG. 2A is a liquid chromatography (LC) diagram obtained from analyzing a prepared fluorescent saccharide-based derivative according to an embodiment of the disclosure.
Figure 2B:
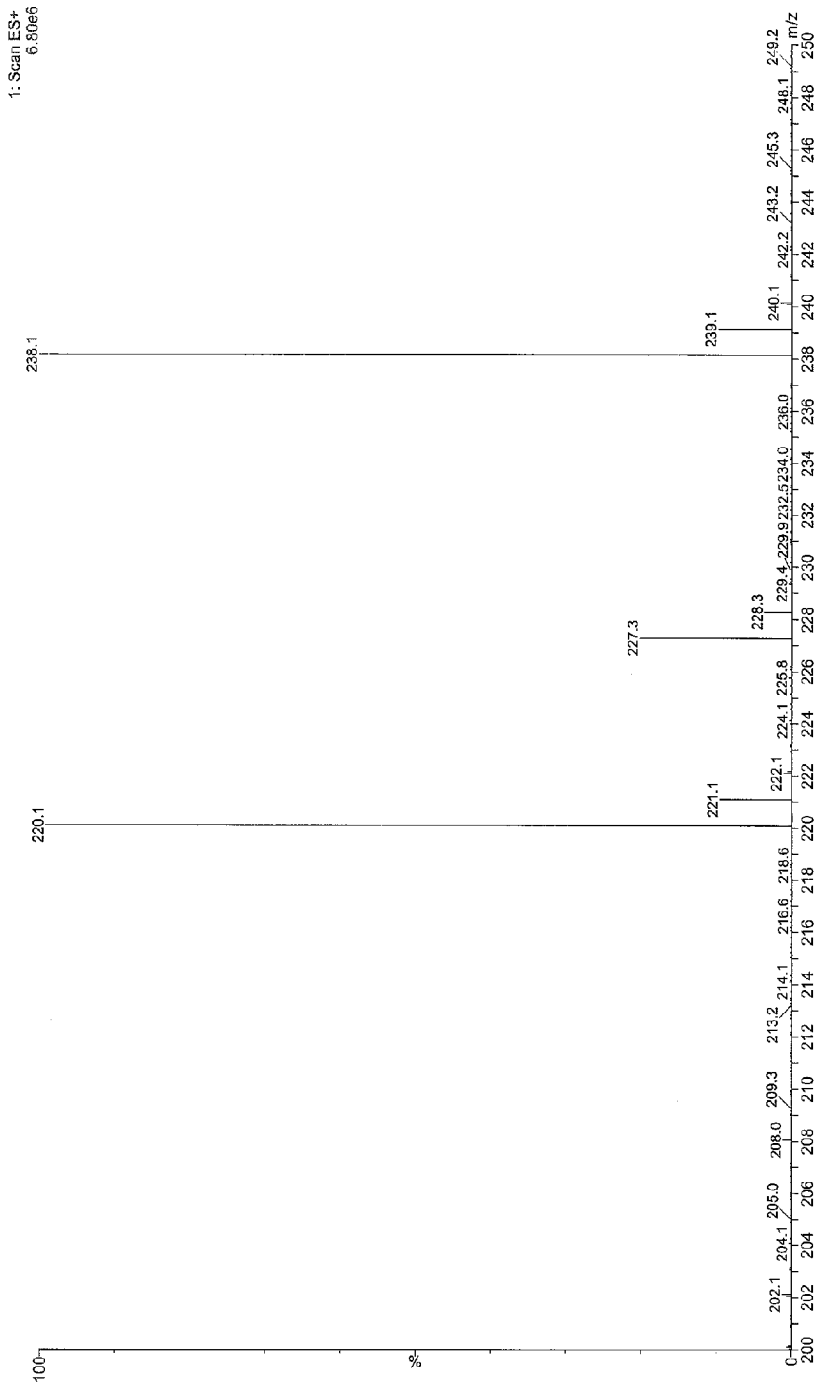
FIG. 2B is a mass spectrometry (MS) diagram obtained from analyzing a prepared fluorescent saccharide-based derivative according to an embodiment of the disclosure.

FIG. 2A is the obtained LC diagram (injection volume: 2 μl; cone voltage: 15 V). Only one apparent peak position exists in the LC diagram of FIG. 2A, confirming the high purity of the obtained product. FIG. 2B is the MS diagram obtained by analyzing the end product (cone voltage: 15 V; m/z range: 200 to 250). The molecular weight of the product is confirmed to be 237 (M+1: 238) from the MS diagram of FIG. 2B, satisfying the molecular characteristics of the desired product in a theoretical model.

(2) Identification of the Functional Group—FT-IR Spectrum

Figure 2C:
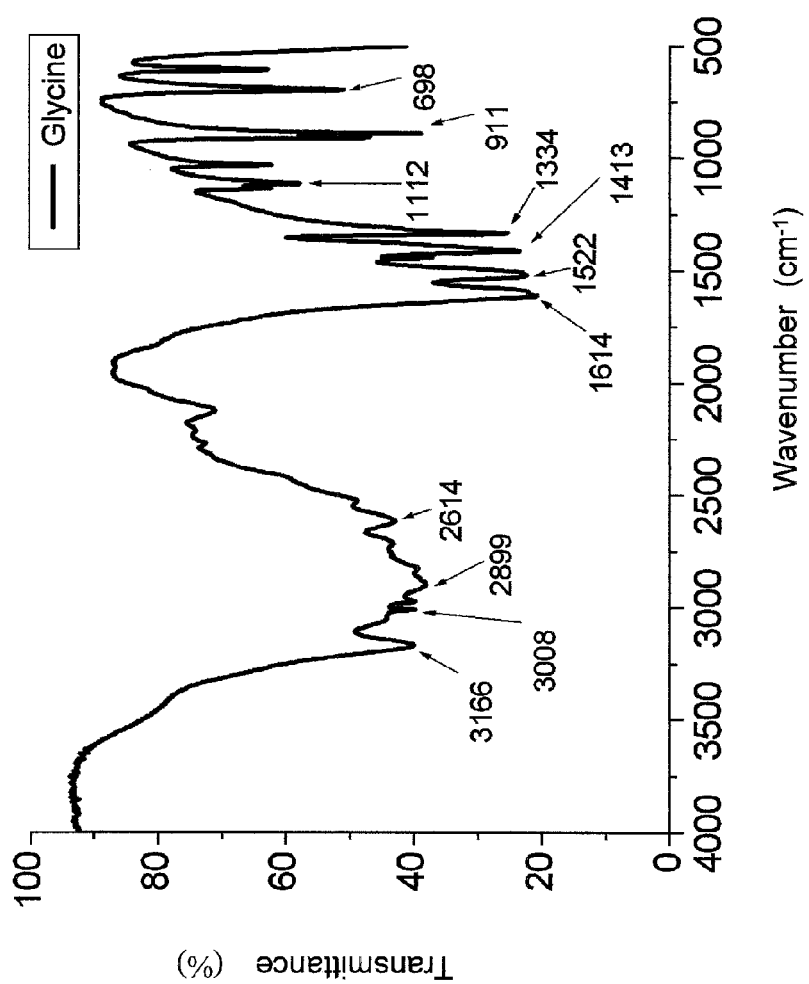
FIG. 2C is a Fourier-transform infrared spectroscopy (FT-IR) diagram of glycine.
Figure 2D:
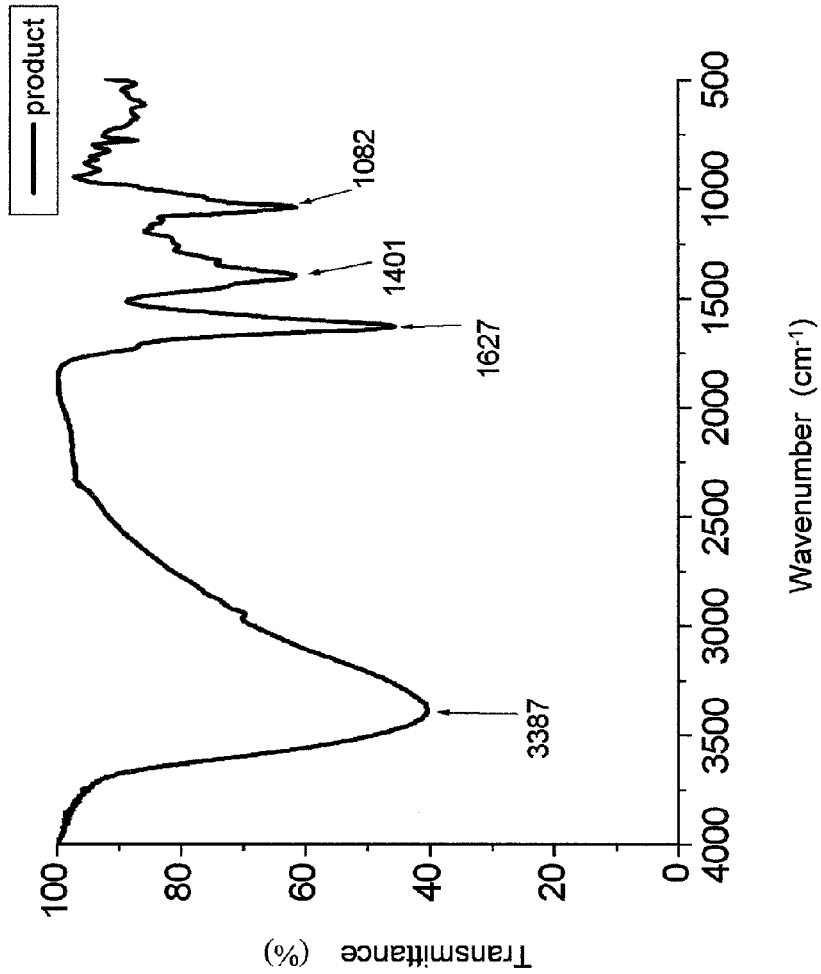
FIG. 2D is an FT-IR diagram obtained from analyzing a prepared fluorescent saccharide-based derivative according to an embodiment of the disclosure.

The functional group of the end product is further identified with the FT-IR spectrum. FIG. 2C is the FT-IR diagram of glycine, and FIG. 2D is the FT-IR diagram of the end product. Referring to FIG. 2C and FIG. 2D, $\delta_{as}$ (N—H) (1614 cm$^{-1}$), $\delta_s$ (N—H) (1522 cm$^{-1}$), ρ (N—H) (1112 cm$^{-1}$), ν (C—N) (1034 cm$^{-1}$) of glycine in the FT-IR diagram disappear after the reaction, and 1627 cm$^{-1}$ expressed in the end product satisfies the characteristic of ν(C=N), showing the end product does in fact have a Schiff base form.

Figure 2E:
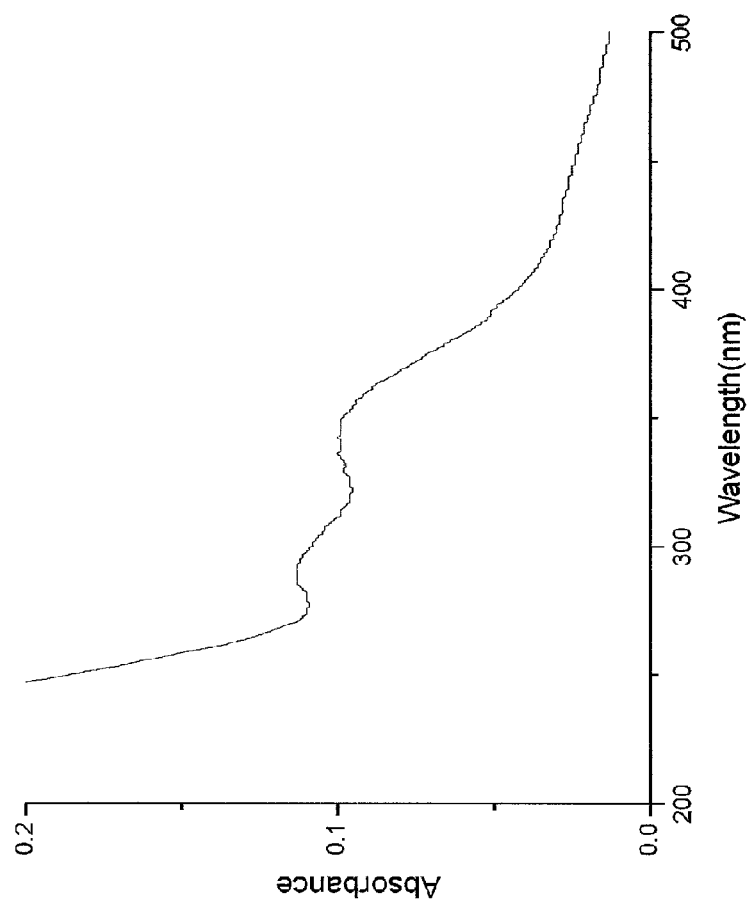
FIG. 2E is a UV absorption spectrum of a prepared fluorescent saccharide-based derivative according to an embodiment of the disclosure.

(3) Optical Properties and Identification of the Functional Group—UV-Vis Spectrum FIG. 2E shows the result of further product identification with the HITACHI U3300 ultraviolet light—UV-Vis spectrometer. Referring to FIG. 2E, it may be acquired that the end product has an apparent peak position near 290 nm and 350 nm, with the former having a peak position matching with the π→π* transition of >C N, and the latter having a peak position matching with the n→π* transition of >C=N. It displays that the end product does have a C=N bond.

Summarizing the LC/MS, FT-IR and UV diagrams, it may be acquired that the synthesized product is D-glucosylglycine and has a Schiff base form.

(4) Identification of Optical Properties—Fluorescent Spectrometer

Figure 2F:
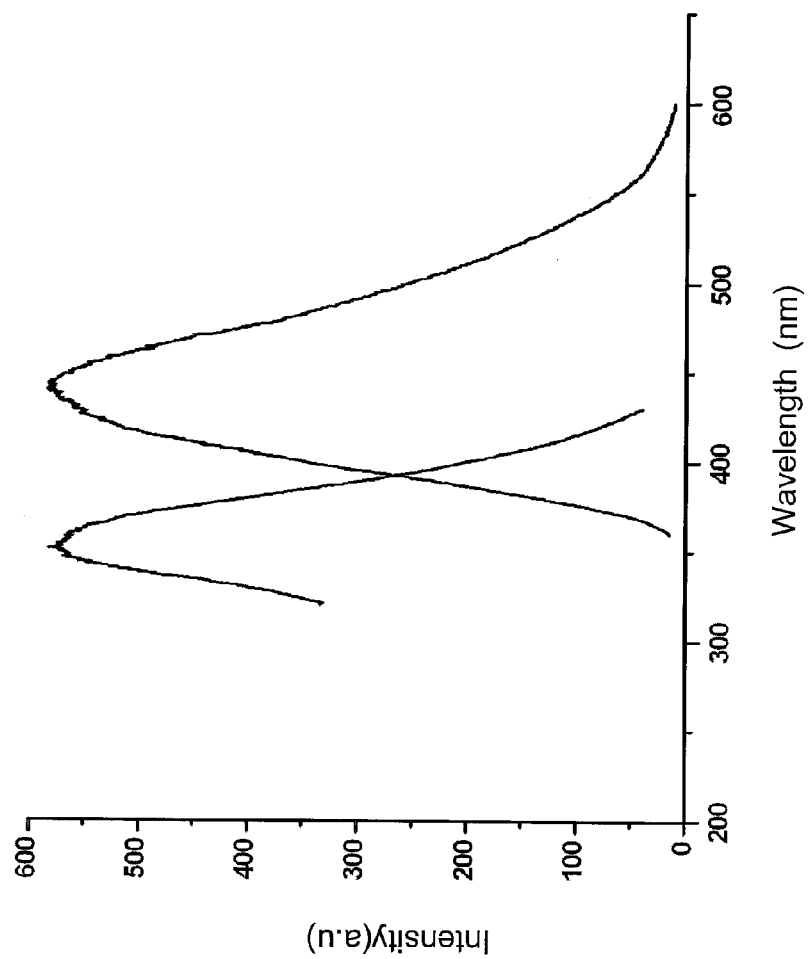
FIG. 2F is a fluorescence excitation spectrum and an emission spectrum of a prepared fluorescent saccharide-based derivative according to an embodiment of the disclosure.
Figure 4:
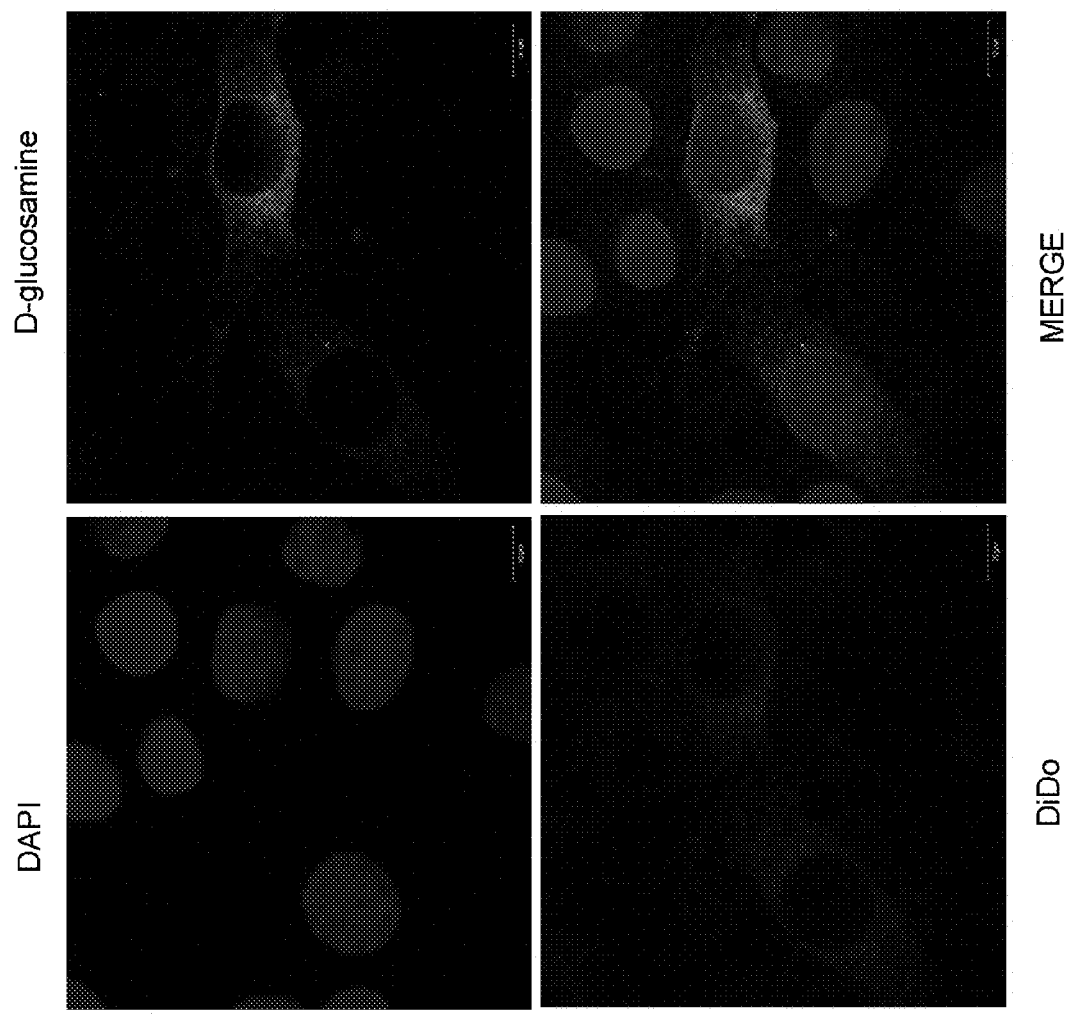
FIG. 4 shows images observed under a laser confocal microscope of using a fluorescent saccharide-based derivative obtained from a self-reaction of D-glucosamine in detection of glioma cancer cells from mixed heterogeneous cells according to an embodiment of the disclosure.
Figure 5:
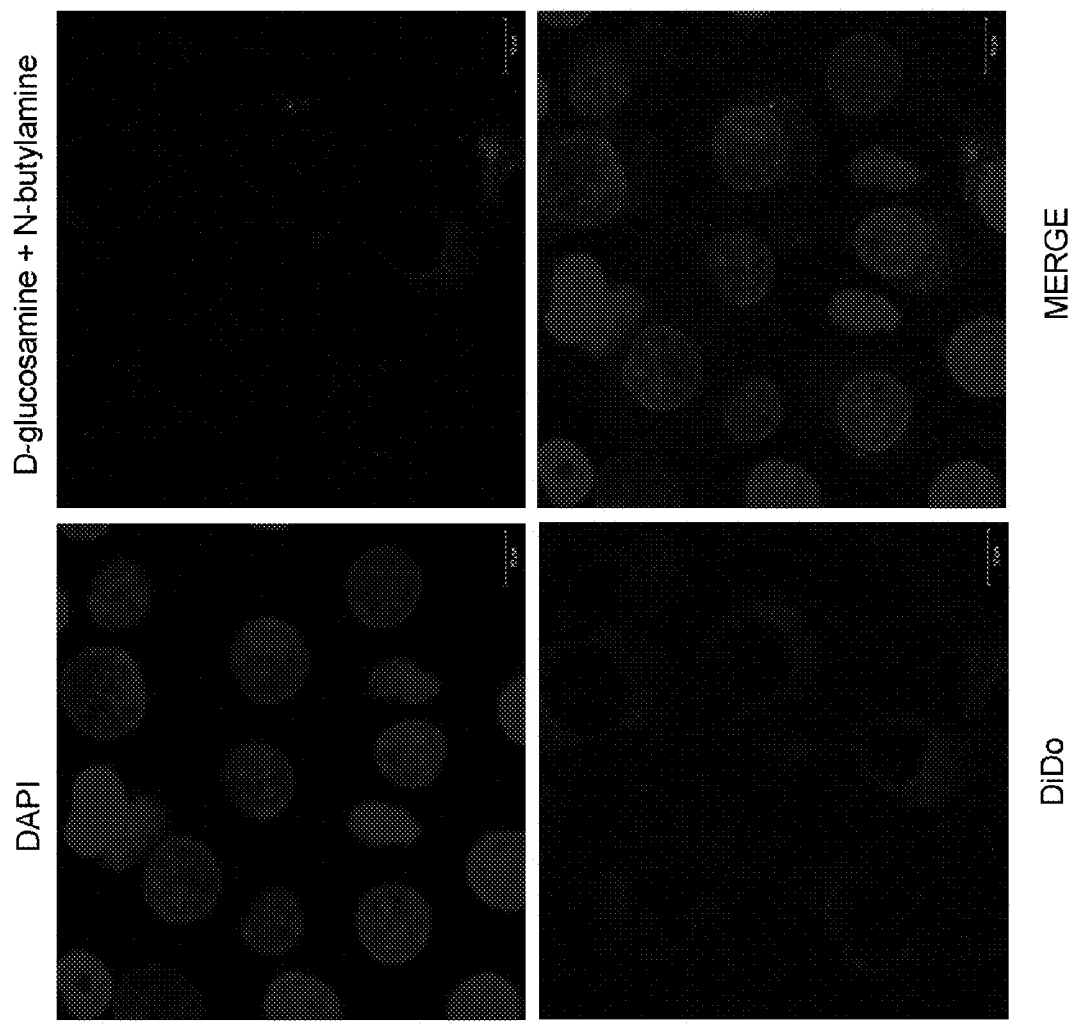
FIG. 5 shows images observed under a laser confocal microscope of using a fluorescent saccharide-based derivative obtained from the reaction between D-glucosamine and n-butylamine in detection of glioma cancer cells from mixed heterogeneous cells according to an embodiment of the disclosure.
Figure 6:
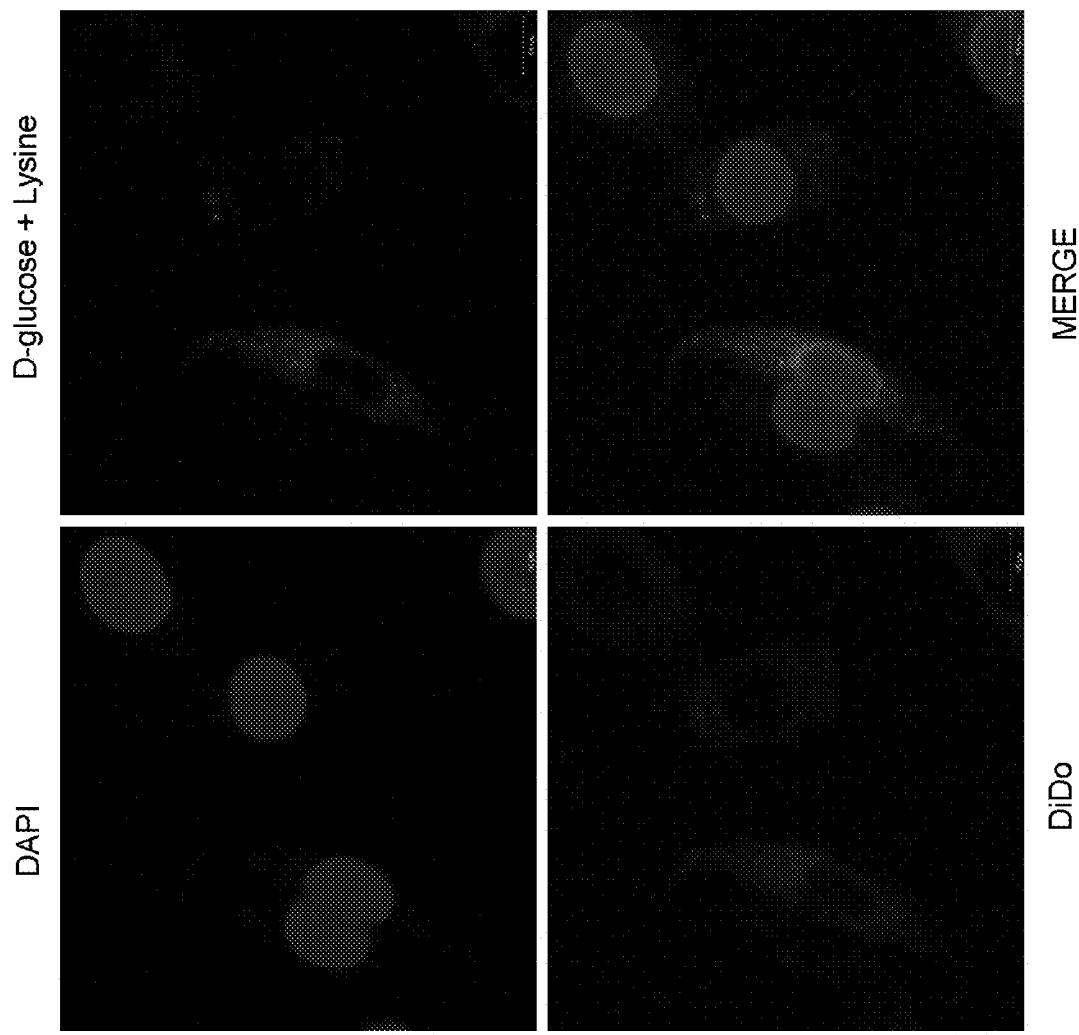
FIG. 6 shows images observed under a laser confocal microscope of using a fluorescent saccharide-based derivative obtained from the reaction between D-glucose and lysine in detection of glioma cancer cells from mixed heterogeneous cells according to an embodiment of the disclosure.
Figure 7:
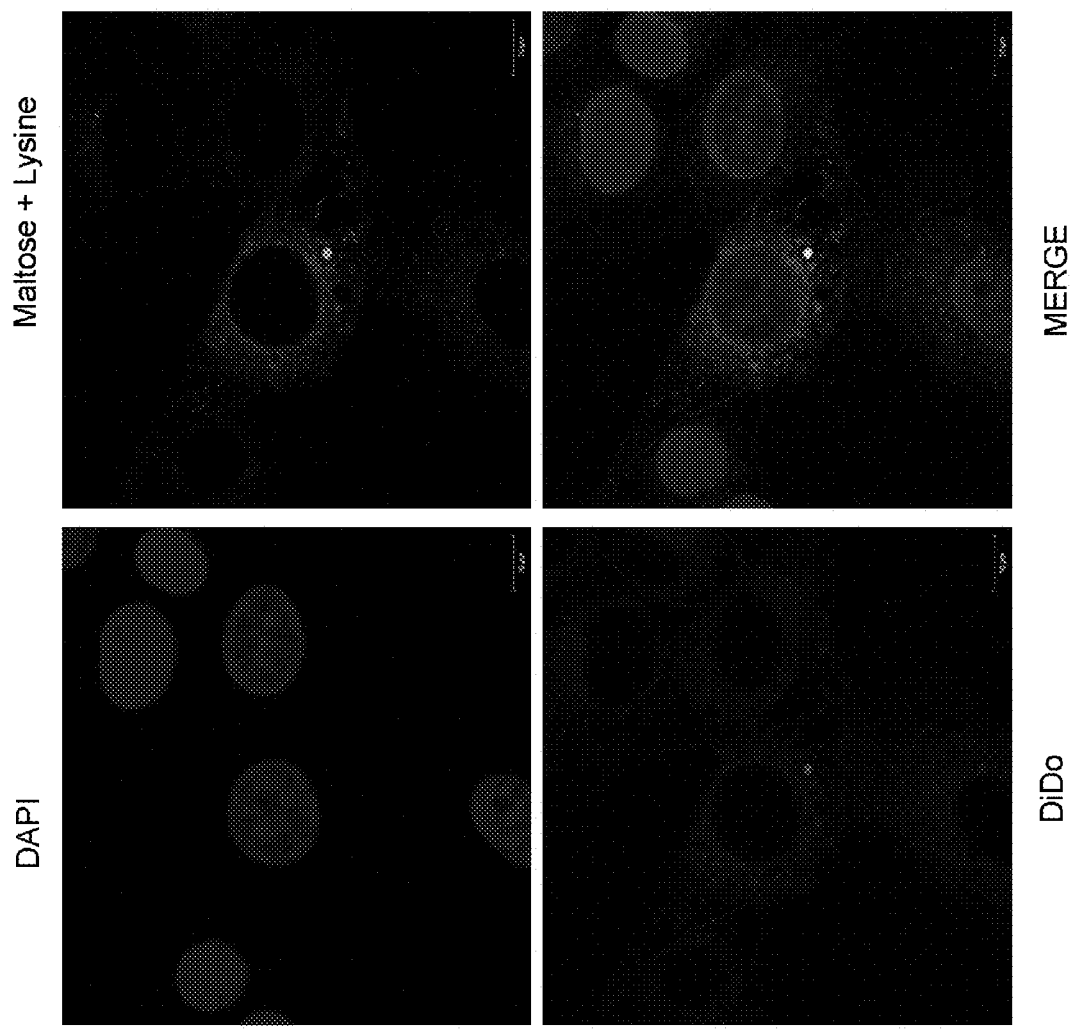
FIG. 7 shows images observed under a laser confocal microscope of using a fluorescent saccharide-based derivative obtained from the reaction between maltose and lysine in detection of glioma cancer cells from mixed heterogeneous cells according to an embodiment of the disclosure.

Moreover, the results of the excitation spectrum and the emission spectrum analyzed with the HITACHI F4500 fluorescent spectrometer of the product are shown in FIG. 2F. It may be acquired from FIG. 2F that the product of the experimental example has an optimal excitation wavelength of 350 nm, and an optimal emission wavelength of 440 nm. Moreover, the excitation wavelength matches with the UV absorption peak, showing that fluorescence is in fact related to the product having the Schiff base form.

«Cellular uptake of Fluorescent Saccharide-Based Derivative Experiment»

To determine if the fluorescent saccharide-based derivative is uptakable by cells, the synthesized glucosylglycine is fed to the fibroblast 3T3 cells.

Experimental Materials

Fibroblast 3T3 cells, RPMI 1640 culture medium, fetal bovine serum, pyruvic acid, glutamic acid, antibiotics, PBS, typsin, trypan blue, 24-well culture plate, paraformaldehyde, and antifade mounting solution.

Experimental Procedure

1. Cultivate the fibroblast 3T3 cells in a DMEM medium (the DMEM medium contains 10% fetal bovine serum, 5 mM pyruvic acid, and antibiotics). The cells are cultivated in an incubator containing 5% $CO_2$.

2. When the cells grow and occupy 80% of the bottom of the culture flask through cell division, suck out the culture medium and wash with 1×PBS, then add 0.05% trypsin to react for 1 minute in order to separate the cells, and add 5 ml culture medium, then centrifuge with 8000 g for 10 minutes.

3. After centrifugation, remove the supernatant, then add 5 ml of culture medium, and evenly mix the cells and the culture medium. Take 30 µl of the cell solution and mix with 270 µl of trypan blue, then take 100 µl and place on a cytometer, and count the cell number using erythrocytomertry.

4. After counting the cells, adjust the cell number to $1\times10^4$ cells/ml, and take 1 ml of the cells and plant into a 24-well culture plate containing a glass slide, then place the cells in a cell incubator at 37° C. and 5% $CO_2$. Incubate for 1 day, and then add 100 µl of 0.5 mg/ml glucosylglycine. After reacting overnight, wash twice with 1×PBS (10 minutes/turn).

5. Add 4% paraformaldehyde to the culture plate, and place in room temperature for twenty minutes to fix the cells, then remove the paraformaldehyde and wash 3 times with 1×PBS (10 minutes/turn).

6. Add 50 µl of antifade mounting solution on the glass slide containing cells to perform mounting, and the result may be observed with a laser confocal microscope and pictures may be taken.

It may be acquired from the experimental results (refer to FIG. 2G) that, cells emit fluorescence after being fed, proving that the fluorescent saccharide-based derivative is uptakable by cells.

EXPERIMENTAL EXAMPLE 2

Identification of Cancer Cells

To further assess the uptake efficiency of fluorescent saccharide-based derivative, a mixed heterogeneous cell model was brought forward and fluorescent saccharide-based derivatives were investigated in the model. Therefore, cancerous rat astrocytoma C6 cells prelabeled with red fluorescent commercial DiDo dye were mixed culture with non-cancerous fibroblasts and fluorescent saccharide-based derivatives were incubated with two heterogeneous cells mixed in varying ratios for cancer cells detection.

Experimental Materials

A. Various Self-Prepared Fluorescent Saccharide-Based Derivatives (1) Fluorescent saccharide-based derivative obtained from the reaction between D-glucose ($6\times10^{-3}$ M) and n-butylamine (0.03 M) at 90° C. lasting 48 hours.

(2) Fluorescent saccharide-based derivative obtained from the self-reaction of D-glucosamine ($1.2\times10^{-2}$ M) at 90° C. lasting 48 hours.

(3) Fluorescent saccharide-based derivative obtained from the reaction between D-glucosamine ($6\times10^{-3}$ M) and n-butylamine (0.03 M) at 90° C. lasting 48 hours.

(4) Fluorescent saccharide-based derivative obtained from the reaction between D-glucose ($6\times10^{-3}$ M) and lysine (0.03 M) at 90° C. lasting 48 hours.

(5) Fluorescent maltose-based derivative obtained from the reaction between maltose ($3\times10^{-3}$ M) and lysine (0.015 M) at 90° C. lasting 48 hours.

B. Cell Strains and Cell Culture Materials

Astrocytoma cells (C6 cell), non-cancerous fibroblast (3T3 cell), RPMI 1640 culture medium, fetal bovine serum, pyruvic acid, glutamic acid, antibiotics, PBS, trypsin, trypan blue, 24-well culture plate, paraformaldehyde, and antifade mounting solution.

Experimental Procedure

1. Separately cultivate the astrocytoma cells (such as C6) and the non-cancerous fibroblast 3T3 cells in a RPMI 1640 and a DMEM medium (the medium contains 10% fetal bovine serum, 5 mM pyruvic acid, 5 mM glutamic acid, and antibiotics), respectively. The cells are cultivated in an incubator containing 5% $CO_2$.

2. When the cells grow to 80% of confluence, remove the culture medium and wash with 1×PBS, then add 0.05% trypsin and react for 1 minute to separate the cells and add 5 ml of culture medium, then centrifuge with 8000 g for 10 minutes.

3. After centrifugation, remove the supernatant, then add 5 ml of culture medium and evenly mix the cells and the culture medium; in particular, conduct the binding reaction of the cancerous astrocytoma cells with long-chain dialkylcarbocyanines (DiDo dye). React for 30 minutes then wash with PBS.

4. Take 30 µl of the cell solution from both C6 and 3T3 cells, and add 270 µl of trypan blue to mix. Take 100 µl and place on a cytometer, and count the cell number using erythrocytomertry.

5. After counting the cells, adjust each of the cell numbers to $1\times10^4$ cells/ml, and remove 0.5 ml of each cells and plant into a 24-well culture plate containing a glass slide, and incubate the C6 cells containing long-chain dialkylcarbocyanines and the 3T3 cells together in an incubator at 37 t and 5% $CO_2$. After incubating for 1 day, add different fluorescent saccharide-based derivatives.

6. After the cells and the fluorescent saccharide-based derivatives react for 16 hours, wash twice with 1×PBS (10 minutes/turn), then add 4% of paraformaldehyde and place in room temperature for twenty minutes to fix the cells. Remove the paraformaldehyde and wash thrice with 1×PBS (10 minutes/turn).

7. Add 50 µl of antifade mounting solution on the glass slide containing cells to perform mounting, and the result may be observed with a laser confocal microscope and pictures may be taken.

FIG. 3 to FIG. 7 respectively contains the images of the fluorescent saccharide-based derivatives of (1) to (5) observed under the laser confocal microscope. As shown in FIG. 3 to FIG. 7, the fluorescent saccharide-based derivatives (1) to (5) may be taken up by cancer cells and emit fluorescence (green). Moreover, cancer cells prelabeled with the DiDo dye emit fluorescence (red). After merging the two images (MERGE), it is observed that cells that do not emit red fluorescence also do not emit green fluorescence. Cells that emit green (and also red) fluorescence are cancer cells.

It is confirmed from the results that the location of cancer cells may be identified by detecting the situation of cells taking up fluorescent saccharide-based derivatives.

EXPERIMENTAL EXAMPLE 3

Detection of Microorganisms

Since microorganisms have the characteristic of requiring carbon sources, they also take up the fluorescent saccharide-based derivative of the disclosure and emit fluorescence. Verification that the characteristics may be used to detect microorganisms is provided in the experimental example.

Experimental Materials

Culture (yeast), glass slide, cover slip, inoculating loop (pin), alcohol lamp, YPD yeast culture medium.

Experimental Procedure

1. Heat the inoculating loop perpendicularly to the alcohol lamp until red-hot to sterilize, then let cool and inoculate a single colony from YPD agar plate with yeast growth. Insert the inoculated yeast colony to test tube containing YPD medium, then put on the covers and place into a 37° C. incubator shaker, incubate for 12 hours.

2. Add the fluorescent glucosamine derivative obtained from the D-glucosamine ($1.2 \times 10^{-2}$ M) after self-reacting for 48 hours at 37° C. to the YPD medium, then place into an incubator shaker and incubate for 2 hours.

3. Add a small amount of sterile water with a dropper onto the glass slide that has been soaked in alcohol and sterilized with flame, then use the inoculating loop (pin) to pick up a small amount of colonies (yeast) after sterilizing the loop with flame, and coat the glass slide with the water by the inoculating loop containing bacteria, and mix the sterile water and the colonies evenly, and let the glass slide dry in a laminar flow.

4. Quickly pass the dried glass slide (with the coated side facing up) over a flame several times to fix, then add the mounting glue, cover with the cover slip, and place under the laser confocal microscope to observe, with the result shown in FIG. 8.

Figure 8:
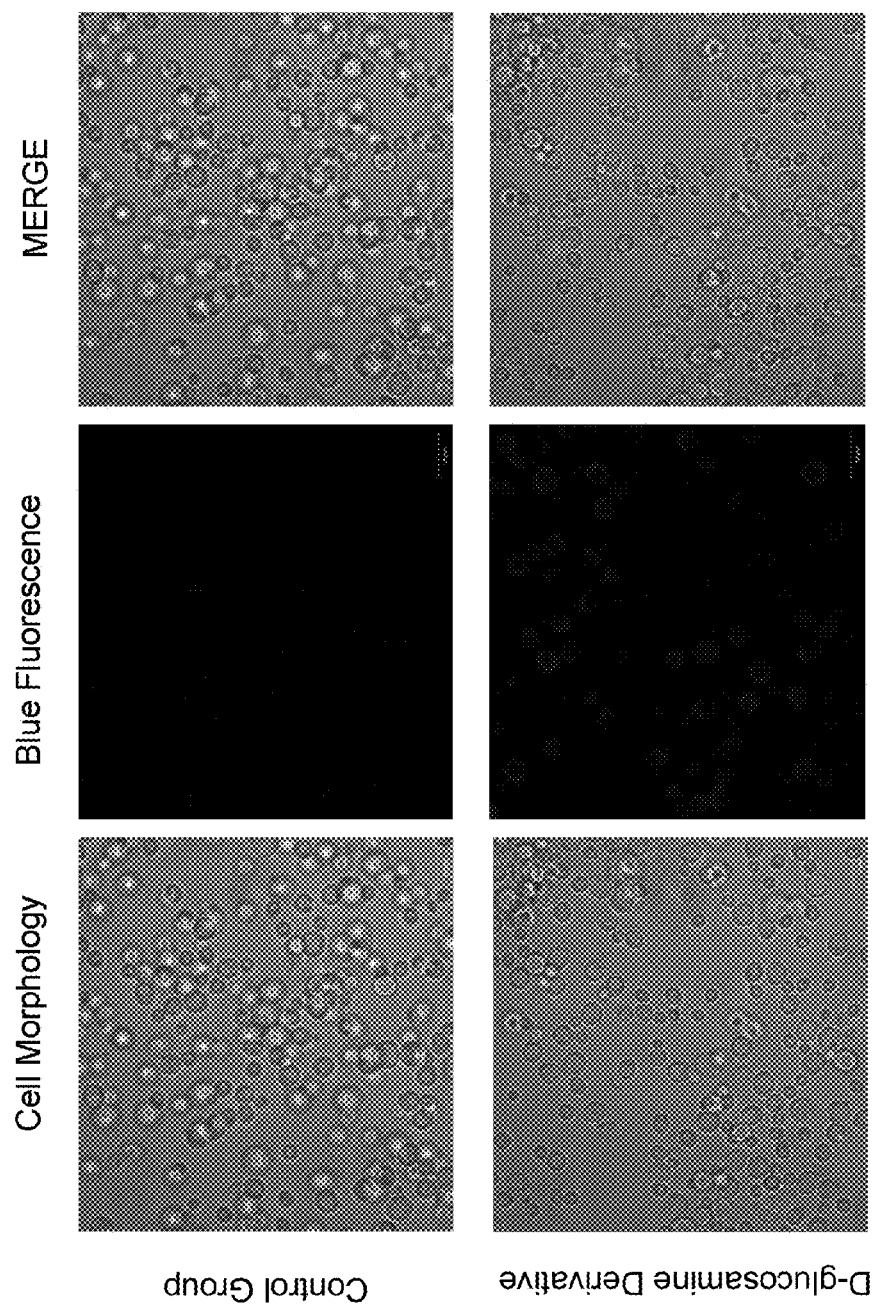
FIG. 8 shows images observed under a laser confocal microscope of using a fluorescent saccharide-based derivative obtained from the reaction between D-glucose and lysine in detection of yeast cells according to an embodiment of the disclosure.

As shown in FIG. 8, bacteria emitting blue fluorescence are observed under a confocal laser confocal microscope, confirming that the presence of microorganisms may be detected by using the method.

EXPERIMENTAL EXAMPLE 4

Application of Cell-Based Screens for Drug Discovery

Figure 9:
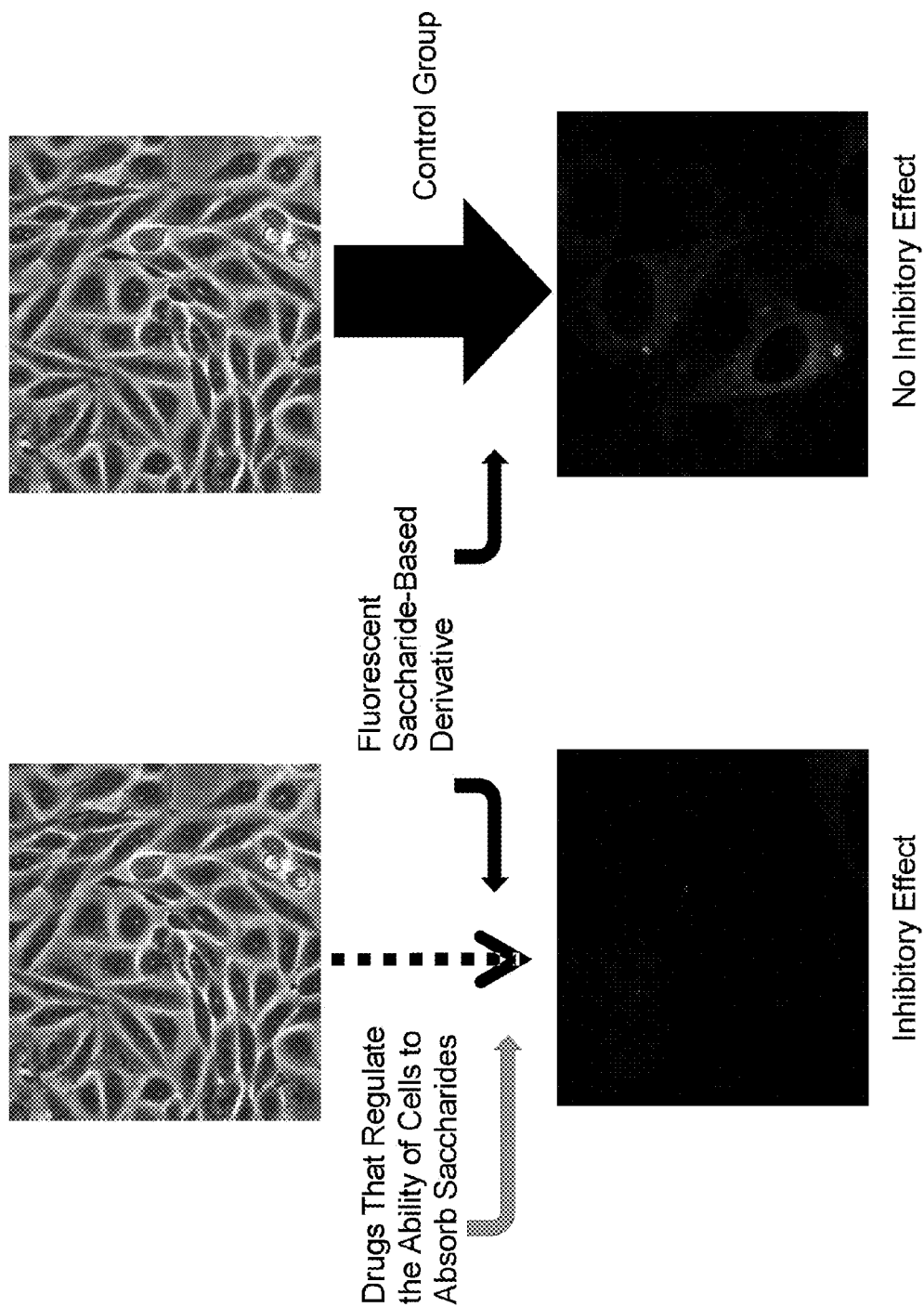
FIG. 9 is a schematic diagram of the reaction mechanism of applying a fluorescent saccharide-based derivative in drug screening according to an embodiment of the disclosure.

FIG. 9 is a schematic diagram of the reaction mechanism of applying a fluorescent saccharide-based derivative in drug screening according to an embodiment of the disclosure. As shown in FIG. 9, cells that are treated (left figure) with 'drugs that regulate the ability of cells to take up saccharides (including saccharide-based molecule uptake inhibitors), have suppressed abilities to take up saccharides, thus showing less fluorescence than the original cells without being treated (right figure). With the principle, the actual abilities of drugs to regulate cell uptake of saccharides may be easily determined by comparing the fluorescence intensities between the processed and unprocessed cells.

EXPERIMENTAL EXAMPLE 5

Simple Environmental Toxicant Detection

In general, the growth of microorganisms is threatened (may even die) in an environment containing biologically toxic substances, resulting in less uptake ability of carbon, and therefore less uptake ability of fluorescent saccharide-based derivatives. With the principle, biological toxicities of samples to be detected may easily be detected by comparison of the expressed fluorescence intensities between the microorganisms after being fed fluorescent saccharide-based derivatives in the samples to be detected and in a normal environment.

Figure 10:
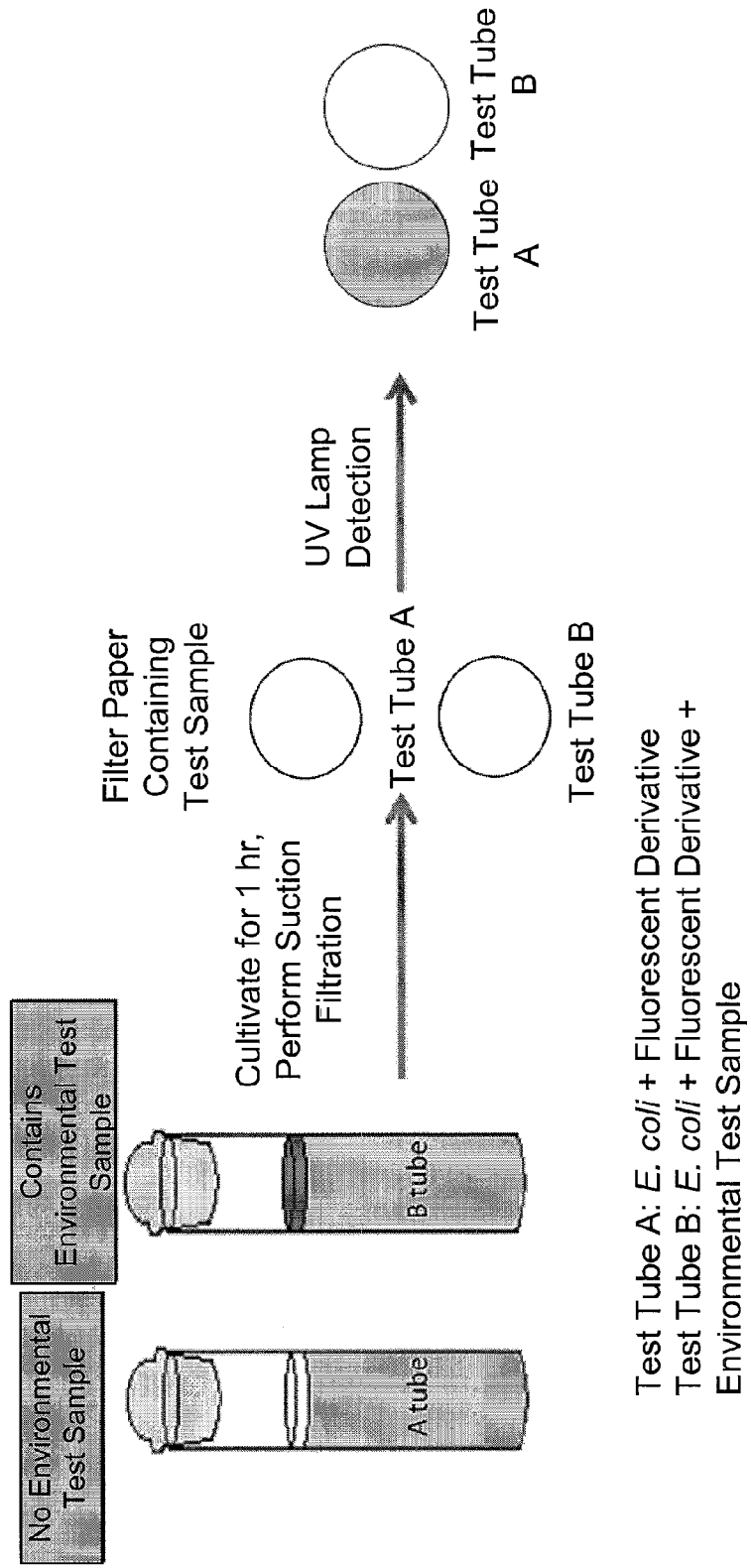
FIG. 10 is a schematic diagram of the operating principle of using a fluorescent saccharide-based derivative to conveniently detect biological toxicants in an environment.

FIG. 10 is a schematic diagram of the operating principle of using a fluorescent saccharide-based derivative to quickly and easily detect toxic substances of biological threat in the environment. As shown in FIG. 10, test tube A and test tube B both contain culture medium, fluorescent saccharide-based derivatives, and a specific amount of *E. coli*, but an environmental test sample is added to test tube B, and test tube A is the control group.

The test tube A and test tube B are placed in an incubator at 37° C. and incubate for 1 hour, then a suction filtration process is performed, and the liquids containing microorganisms are separately poured from the test tubes into filters containing filter papers (with a filter diameter of less than 0.2 μm). The microorganisms would stay on the filter papers after filtration. Then, the filter papers containing microorganisms are irradiated with a fixed or movable ultraviolet lamp, and the fluorescence intensities of the two are compared to determine the presence of biologically toxic substances in the environmental test sample.

If the environmental test sample does not contain biologically toxic substances, the fluorescence intensities of the filter papers obtained from test tube A and test tube B should be similar, and if the environmental test sample contain biologically toxic substances, the fluorescence intensity of the filter paper obtained from test tube B containing environmental test sample would be weaker. A simple and fast environmental toxicant detection may be accomplished with the method.

In summary, detecting cells with the fluorescent saccharide-based derivative provided in the disclosure may achieve a fluorescent detection method that is fast, simple, low costing, non-toxic, and has good biocompatibility. Moreover, since it has good biocompatibility, it does not poison cells when applied in biomedical testing, therefore it does not cause cell damage, and so is very suitable for fields such as cancer cell detection, microorganism detection, and drug screening.

Although the disclosure has been described with reference to the above embodiments, it will be apparent to one of the ordinary skill in the art that modifications and variations to the described embodiments may be made without departing from the spirit and scope of the disclosure. Accordingly, the scope of the disclosure will be defined by the attached claims not by the above detailed descriptions.

What is claimed is:

1. A method of detecting cells using a fluorescent saccharide-based derivative, including:
   incubating at least one sample with a fluorescent saccharide-based derivative;
   emitting an excitation light to the at least one sample; and
   detecting fluorescence emitted from the at least one sample,
   wherein the fluorescent saccharide-based derivative is obtained from a reactive material through an imine formation reaction, and the reactive material is selected from a composition (A) or a composition (B):
   the composition (A) comprises a reducing sugar compound and an amino group-containing compound having at least one primary amino group;

the composition (B) comprises an amino sugar compound and a carbonyl group-containing compound, wherein the amino sugar compound has at least one primary amino group.

2. The method of claim 1, wherein the reducing sugar compound is selected from the group consisting of glucose, maltose, fructose, lactose, galactose, mannose, cellobiose, xylose, arabinose, ribose, deoxyribose, dextrin, D-glucosamine, and N-acetyl-glucosamine.

3. The method of claim 1, wherein the amino group-containing compound is selected from an amino acid or an alkyl amine.

4. The method of claim 3, wherein the amino group-containing compound is selected from the group consisting of butylamine, octylamine, 1-dodecylamine, 1-hexadecylamine, 1,6-hexadiamine, glycine, alanine, valine, leucine, isoleucine, phenylalanine, tryptophan, tyrosine, aspartic acid, histidine, asparagine, glutamic acid, lysine, glutamine, methionine, arginine, serine, threonine, cysteine, and proline.

5. The method of claim 1, wherein the amino sugar compound is selected from the group consisting of D-glucosamine, galactosamine, and chitosan.

6. The method of claim 1, wherein the carbonyl group-containing compound is selected from the group consisting of acetone, isovaleraldehyde, D-glucosamine, and N-acetyl-glucosamine.

7. The method of claim 1, wherein the amino sugar compound and the carbonyl group-containing compound are the same compound.

8. The method of claim 1 for detection of cancer, wherein location of a cancer cell in the at least one sample is identified by detecting the fluorescence emitted from the at least one sample.

9. The method of claim 1 for detection of microorganisms, wherein presence of a microorganism in the at least one sample is confirmed by detecting the fluorescence emitted from the at least one sample.

10. The method of claim 1 for screening drugs related to regulation of the ability of cells to take up saccharides, determined by comparing intensities of fluorescence between at least two cell samples, wherein one sample is untreated and at least one sample includes cells treated with a drug related to cells' ability to take up saccharides.

11. The method of claim 1 for detection of environmental toxicants, wherein the at least one sample includes two samples each containing a microorganism, and one of the two samples further contains an environmental test sample, and presence of a biologically toxic substance in the environmental test sample is determined by comparing intensities of the fluorescence between the two samples.

* * * * *